US012178509B2

(12) United States Patent
Alvarez et al.

(10) Patent No.: US 12,178,509 B2
(45) Date of Patent: Dec. 31, 2024

(54) METHOD, SYSTEM AND APPARATUS FOR DIAGNOSTIC ASSESSMENT AND SCREENING OF BINOCULAR DYSFUNCTIONS

(71) Applicant: New Jersey Institute of Technology, Newark, NJ (US)

(72) Inventors: Tara Lynn Alvarez, Whippany, NJ (US); Chang Yaramothu, Fanwood, NJ (US); John Vito d'Antonio-Bertagnolli, Mount Laurel, NJ (US); Mitchell Scheiman, Bala Cynwyd, PA (US)

(73) Assignee: New Jersey Institute of Technology, Newark, NJ (US)

( * ) Notice: Subject to any disclaimer, the term of this patent is extended or adjusted under 35 U.S.C. 154(b) by 966 days.

(21) Appl. No.: 17/253,300

(22) PCT Filed: Jun. 18, 2019

(86) PCT No.: PCT/US2019/037732
§ 371 (c)(1),
(2) Date: Dec. 17, 2020

(87) PCT Pub. No.: WO2019/246098
PCT Pub. Date: Dec. 26, 2019

(65) Prior Publication Data
US 2021/0275013 A1    Sep. 9, 2021

Related U.S. Application Data

(60) Provisional application No. 62/686,406, filed on Jun. 18, 2018.

(51) Int. Cl.
*A61B 3/08*    (2006.01)
*A61B 3/00*    (2006.01)
(Continued)

(52) U.S. Cl.
CPC .............. *A61B 3/08* (2013.01); *A61B 3/005* (2013.01); *A61B 3/032* (2013.01); *A61B 3/113* (2013.01); *A61B 5/7267* (2013.01); *G02B 30/36* (2020.01)

(58) Field of Classification Search
None
See application file for complete search history.

(56) References Cited

U.S. PATENT DOCUMENTS

| | | |
|---|---|---|
| 9,039,180 B2 | 5/2015 | Brown, Jr. et al. |
| 2012/0183191 A1* | 7/2012 | Nakamura ............ G16H 30/40 382/128 |

(Continued)

FOREIGN PATENT DOCUMENTS

WO    WO 2017/015603 A1    1/2017

OTHER PUBLICATIONS

Extended European Search Report dated Feb. 28, 2022 for European Patent Application 19821810.9.

(Continued)

*Primary Examiner* — Benjamin S Melhus
*Assistant Examiner* — Samuel C Kim
(74) *Attorney, Agent, or Firm* — McCarter & English, LLP

(57) ABSTRACT

Exemplary embodiments relate to systems, methods, and apparatus to objectively assess binocular dysfunction for screening, diagnoses, and evaluation of vision/oculomotor function before, during, and after various forms of therapeutic interventions. Systems and methods diagnose and assess binocular dysfunction objectively and automatically, can render a visual stimulus on one or more displays, and can control accommodative and proximal vergence stimulation of a user's eyes.

24 Claims, 8 Drawing Sheets

(51) Int. Cl.
*A61B 3/032* (2006.01)
*A61B 3/113* (2006.01)
*A61B 5/00* (2006.01)
*G02B 30/36* (2020.01)

(56) References Cited

U.S. PATENT DOCUMENTS

| | | | |
|---|---|---|---|
| 2013/0176534 A1* | 7/2013 | Frankfort | A61B 3/0025 |
| | | | 351/209 |
| 2014/0160432 A1 | 6/2014 | Brown, Jr. et al. | |
| 2014/0171756 A1* | 6/2014 | Waldorf | A61B 3/032 |
| | | | 600/301 |
| 2015/0070349 A1* | 3/2015 | Shinomiya | A61B 3/08 |
| | | | 351/201 |
| 2015/0317956 A1* | 11/2015 | Lection | G09G 5/38 |
| | | | 345/633 |
| 2015/0338915 A1 | 11/2015 | Publicover et al. | |
| 2016/0320620 A1* | 11/2016 | Maimone | G02B 6/0008 |
| 2017/0293356 A1* | 10/2017 | Khaderi | G02B 27/0172 |
| 2017/0365101 A1 | 12/2017 | Samec et al. | |
| 2018/0090229 A1* | 3/2018 | Sanyal | A61B 5/0024 |
| 2019/0004600 A1* | 1/2019 | Wu | G06T 7/70 |
| 2021/0014473 A1* | 1/2021 | Hua | G02B 27/0172 |

OTHER PUBLICATIONS

PCT International Search Report and Written Opinion dated Sep. 13, 2019.
Office Action from related European Patent Application 19821810.9 issued Mar. 27, 2024.

* cited by examiner

400

METHOD, SYSTEM AND APPARATUS FOR DIAGNOSTIC ASSESSMENT AND SCREENING OF BINOCULAR DYSFUNCTIONS

CROSS REFERENCE TO RELATED APPLICATIONS

The present application claims priority to and the benefit of U.S. Provisional Application No. 62/686,406, filed on Jun. 18, 2018, the content of which is incorporated by reference herein in its entirety.

STATEMENT REGARDING FEDERALLY SPONSORED RESEARCH

This invention was made with government support under Grant No. CBET1228254 awarded by the National Science Foundation and under Grant No. R01EY023261 awarded by the National Institutes of Health. The government has certain rights in the invention.

FIELD OF THE DISCLOSURE

The present disclosure relates to systems and methods for a diagnostic assessment and screening of a binocular dysfunction.

BACKGROUND

Symptomatic binocular dysfunctions are present in about 4.2% to 17.6% of the general population and between 40% and 50% of the brain injury population. Some examples of binocular dysfunctions include, but are not limited to, strabismus, convergence insufficiency (CI), convergence excess, divergence insufficiency, and divergence excess. The visual symptoms of binocular dysfunction can be exacerbated by, for example, extensive use of hand held electronic devices (e.g., smart phones, tablets, etc.) as well as by any near visual tasks (e.g., reading, computer work, etc.)—adversely impacting occupational and recreational activities of those suffering from binocular dysfunction.

Additionally, virtual reality (VR) is becoming popular for entertainment and education and people with binocular dysfunction may experience more symptoms when attempting to use VR compared to those without binocular dysfunction. When engaged in reading or other near work, asthenopic symptoms associated with binocular dysfunction can include, but are not limited to, double/blurred vision, eyestrain, visual fatigue, having to re-read text, reading slowly, the perception of text floating and headaches, which may negatively impact activities of daily living. Vision therapy is one therapeutic intervention that is commonly used to treat binocular dysfunction.

CI is a binocular vision disorder characterized by a tendency for the eyes to drift outward (exophoria) at near compared to far visual space, a reduced near point of convergence, and inadequate compensatory ability to align the eyes. Fixation disparity is the error or the difference between where the eyes are fixating and where the object upon which the user is trying to fixate is located. Fixation disparity is typically larger in patients with CI compared to binocularly normal controls. Symptoms experienced by a person with CI can include blurry or double vision, headaches, eye strain, and/or difficulty sustaining attention during reading and other near work. Convergence is the inward rotation of the eyes to aim the eyes at an object or objects that are located near to the person and is needed to sustain vision when looking at objects located near to the person, such as when a person is reading or working on a computer. People with CI may experience visual symptoms within a few minutes of performing a near visual task. This is especially true for people with brain injuries including concussion(s) and associated binocular dysfunction.

While screening tools are available, these techniques are subjective and require clinical experience to accurately measure oculomotor function. There is a need for systems and methods to objectively measure oculomotor function to screen for binocular dysfunction for use by both eye care and non-eye care professionals.

SUMMARY

Exemplary embodiments of the present disclosure relate to systems, methods, and apparatus to objectively assess binocular dysfunction for screening, diagnoses, and evaluation of vision/oculomotor function before, during, and after various forms of vision therapies. The exemplary embodiments can be used by various types of healthcare professionals, including, but not limited to, the following: a school nurse, an occupational, physical, or vision therapist, a pediatrician, a family physician, a sports medicine clinician, a sports trainer, a coach, an optometrist, or an ophthalmologist.

A head mounted display can be used within this system. The visual stimuli can be presented to the left, right, or both eyes within the head mounted display. Exemplary embodiments of the present disclosure can quantify near point of convergence, positive and negative fusional vergence range, dissociated and associated phoria, fixation disparity, vergence facility, horizontal/vertical saccade eye movements, smooth pursuit eye movements, vergence eye movements oculomotor/binocular endurance, ability to adapt through an oculomotor learning protocol and other optometric measures. Furthermore, in some embodiments, velocity, accuracy, and precision of each vergence eye movement can be quantified. Embodiments of the present disclosure can determine quality of binocular coordination, determine which eye has a lower peak velocity (slower), and then dynamically adjust the visual stimulation within a therapeutic platform to improve symmetrical binocular coordination of the two eyes.

Some patients also have sensory dominance where one eye perceives a visual stimulus or visual object better with one eye compared to the other eye. This visual sensation is common when patients experience suppression. If patients are expressing visual suppression, exemplary embodiments of the present disclosure can adjust the visual stimuli rendered in the virtual/augmented/mixed settings so that the non-dominant eye sees a stronger visual stimulus, which means an image that may be perceived as brighter or with greater clarity compared to the dominant eye.

The visual stimuli implemented via exemplary embodiments of the present disclosure can use a Gabor Patch and/or small targets, such as a small letter to reduce accommodative cues. It will be understood that other forms of visual stimulus can be used. The Gabor Patch is composed of multiple differences of Gaussian stimuli known to reduce accommodative cues.

Embodiments of an oculomotor assessment software platform (OASP) can evoke disparity vergence, while keeping accommodative cues minimal, and can be used for therapeutic intervention in users with binocular vision dysfunction. Embodiments of the OASP can integrate eye movement position and dynamically modify the visual stimulus rendered in the OASP based upon the user's current eye position. Embodiments of the OASP can be configured to better assess a user's attention as compared to conventional clinical therapeutic interventions.

In accordance with embodiments of the present disclosure, a system for observing oculomotor function of a user is disclosed. The system includes a head mounted display and a computing system. The head mounted display configured to generate a stereoscopic effect viewable by the user. The computing system in communication with the head mounted display. The computing system interacts with the head mounted display to render visual stimulus with the head mounted display, adjust the visual stimulus to elicit a response from a visual system of the user, objectively measure a plurality of oculomotor characteristics of the user based on the response, and generate an oculomotor function assessment by combining the plurality of oculomotor characteristics.

In accordance with embodiments of the present disclosure, a method observing oculomotor function of a user is disclosed. The method includes rendering visual stimulus with a head mounted display using a stereoscopic effect, adjusting, by a computing system, the visual stimulus to elicit a response from a visual system of a user wearing the head mounted display, objectively measuring a plurality of oculomotor characteristics of the user based on the response and an interaction between the head mounted display and the computing system, and generating an oculomotor function assessment by combining the plurality of oculomotor characteristics.

In accordance with embodiments of the present disclosure, a non-transitory computer-readable medium storing instructions is disclosed that when executed by a processing device causes the processing device to implement a method including rendering visual stimulus with a head mounted display using a stereoscopic effect; adjusting the visual stimulus to elicit a response from a visual system of a user wearing the head mounted display; objectively measuring a plurality of oculomotor characteristics of the user based on the response and an interaction between the head mounted display and the computing system; and generating an oculomotor function assessment by combining the plurality of oculomotor characteristics.

In accordance with embodiments of the present disclosure, a method for diagnosing and assessing binocular dysfunction objectively and automatically is disclosed. The method can include rendering a visual stimulus on one or more displays and controlling accommodative and proximal vergence stimulation of a user's eyes via embodiments of the OASP. Embodiments of the OASP can be rendered by a head mounted display. The OASP can be rendered on a head mounted display integrated eye tracking hardware and software. The OASP can additionally be rendered in both virtual reality, augmented reality, and mixed reality settings. The fast-fusional disparity vergence system is composed of a preprogrammed and feedback-controlled component, which can be assessed objectively by the OASP.

In accordance with embodiments of the present disclosure, a left eye or a right eye of the user can be asymmetrically or symmetrically stimulated via embodiments of the OASP to objectively measure peak velocity differences between the left and right eyes. A magnitude of asymmetrical stimulation can be derived from a position of the left and right eyes. The magnitude of asymmetrical stimulation can dynamically change to assess visual suppression.

In accordance with embodiments of the present disclosure, real-time physical eye movements of the left and right eyes of the user can be detected and can be used as inputs for the OASP. A point in a three-dimensional virtual/augmented/mixed reality space to which the user's left and right eyes are fused can be determined based on the real-time physical eye movements. Quantification of measures can also potentially be recorded through user feedback in devices and head mounted displays without eye tracking.

In accordance with embodiments of the present disclosure, a method is disclosed for diagnosing and assessing binocular dysfunction. The method can include fitting a user with a head mounted display configured to render an OASP and to limit or control accommodative stimulation and proximal vergence stimulation, stimulating disparity vergence symmetrically and asymmetrically via the virtual reality software. The left eye and the right eye are asymmetrically stimulated based on an asymmetrical peak velocity difference between the left and right eyes. The method can further include the step of asymmetrically stimulating the left eye or the right eye of the user via the OASP rendered by the head mounted display to limit visual suppression. The OASP can be rendered stereoscopically to render the virtual/augmented/mixed reality software in three-dimensional virtual space.

The head mounted display can include a right eye display and a left eye display configured to render OASP and can include a right eye image capturing device disposed proximate to the right eye display and a left eye image capturing device disposed proximate to the left eye image capturing device, and the method can further include determining the asymmetrical peak velocity difference between the left and right eyes based in images of the left and right eyes captured by the left and right image capturing devices and the left and right eyes move in response to viewing the left and right eye displays. A focal length between the right eye and the left eye display is fixed when the head mounted display is fitted to the user's head. The method can also include dynamically adjusting a magnitude of the asymmetrical stimulation in the OASP to limit visual suppression.

In accordance with embodiments of the present disclosure, a system is disclosed for objectively measuring and assessing binocular function that can be used to diagnose a binocular dysfunction. The system can include a computing system and a head mounted display. The computing system is configured to execute the OASP. The head mounted display is operatively coupled to the computing system. The head mounted display can include a left eye display; a right eye display; one or more display controllers configured to render images on the left eye display and the right eye display of the head mounted display to generate a stereoscopic effect; a first image capturing device disposed proximate to the left eye display; and a second image capturing device disposed proximate to the right eye display. The first image capturing device is configured to capture images of a left eye of a user of the head mounted display and the second image capturing device is configured to capture images of a right eye of the user.

An embodiment of a computing system outputs the visual stimuli and visual stimuli sequence to the head mounted display as well as analyzes the objectively eye movement data. The head mounted display outputs positions of the right and left eyes based on the images captured by the first and second image capturing devices and the computing system controls OASP. The left and right eye displays can render the visual stimuli to assess the preprogrammed and feedback portion of disparity vergence, the potential asymmetrical between the left and right eye movement, and objectively measure common clinical parameters/characteristics. Common clinical vision parameters include but are not limited to the following: near point of convergence, positive and negative fusional vergence range, dissociated and associated phoria, fixation disparity, vergence facility, horizontal/vertical saccades eye movements, smooth eye movements, oculomotor/binocular endurance, and oculomotor adaptation through an oculomotor learning protocol.

Any combination and/or permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

So that those having ordinary skill in the art will have a better understanding of how to make and use the disclosed systems and methods, reference is made to the accompanying figures wherein.

DETAILED DESCRIPTION

Figure 1:
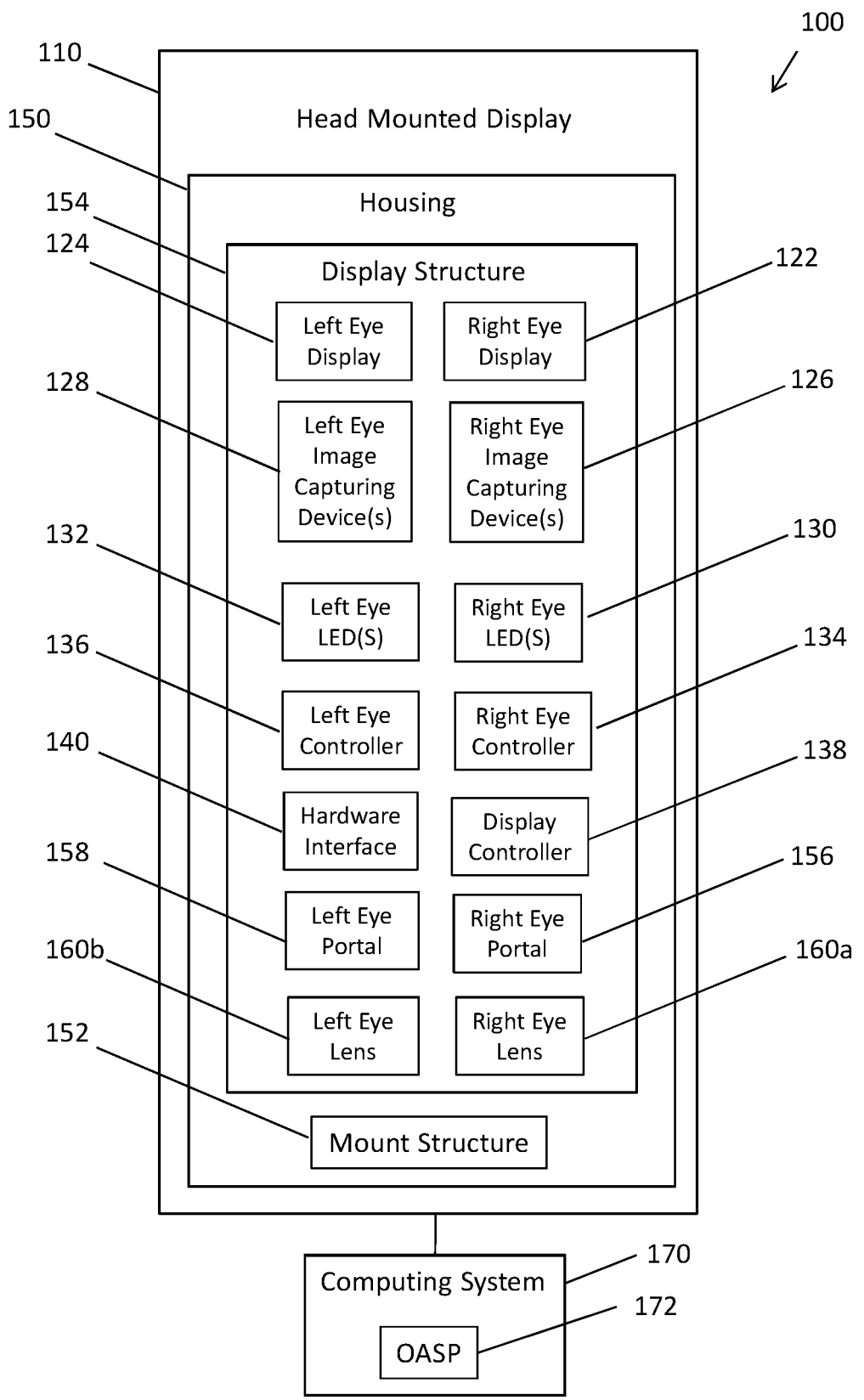
FIG. 1 depicts a block diagram of an exemplary oculomotor assessment system in accordance with exemplary embodiments of the present disclosure.

Exemplary embodiments of the present disclosure objectively assess binocular function using eye tracking. Near point of convergence (NPC) is defined as the closest point along midline where a person can no longer maintain binocular vision. Visual stimuli (one to the left eye and one to the right eye) can be programmed into a virtual reality head mounted display where the OASP can monitor eye alignment. The OASP can objectively determine via eye tracking when binocular fusion is no longer occurring and save this position as the subject's NPC.

Another embodiment of the present disclosure is to objectively assess binocular range analogous to positive and negative fusional range measured clinically. An image can be presented to the left and right eye where one eye's visual stimulus is maintained. The other eye would have the image move outward analogous to base out prism or inward analogous to a base in prism. The prismatic effect achieved by moving one of the visual stimuli can be increased and eye position can be monitored. The OASP can determine objectively the greatest prism strength through which a subject can maintain fusion. Once fusion is lost and diplopia occurs, the OASP can determine objectively the amount of prism strength through which a subject can regain fusion. These data can be saved as positive and negative fusional range.

Exemplary embodiments also include measuring the resting position of the eye when the other eye has no visual stimulus (a dark screen). One embodiment can be the left eye viewing a visual stimulus while the right eye has no visual target and decays to a resting position. The resting position of the right eye would objectively be measured with an eye tracker. These data would be saved as the dissociated phoria. In some embodiments, the computing system can control the head mounted display so that the left and right eyes are shown independent images and the amount of prismatic demand (measured within the head mounted display as the offset of images shown to the eyes) to reduce error (also called fixation disparity) is measured as the associated phoria. In some embodiments, the steady state position of the eye position is measured by the system to measure fixation disparity. Fixation disparity can be measured as the difference between where the actual target is located and where the eyes are fixating.

Exemplary embodiments of the present disclosure can utilize a head mounted display to generate the 3D vision (e.g., using the stereoscopic effect), where each eye receives an image of the same object or scene at slightly different angles or points-of-view and a computing system. The head mounted display provides a constant focal length from the patient's eye, and thereby keeps accommodative stimulation virtually constant. Use of visual stimuli [e.g., such as Gabor patches, which use the Difference of Gaussian (DoG) or small letters] in the images displayed to the user via the head mounted display can further reduce accommodative stimulation. Embodiment of the systems and methods described herein can include a visual display, a head mounted display with or without eye tracking, a computer, and an oculomotor assessment software platform for eye movement analysis and assessment.

FIG. 1 shows an exemplary oculomotor assessment system 100 in accordance with exemplary embodiments of the present disclosure. The oculomotor assessment system 100 can include a head mounted display 110 and a computing system 170. The head mounted display 110 and the computing system 170 can be communicatively coupled to each other via wireless or wired communications such that the head mounted display 110 and the computing system 170 can interact with each other to implement a virtual reality environment for oculomotor assessment. For example, embodiments of the oculomotor assessment system 100 can be configured to provide a virtual reality environment to assess oculomotor function associated with binocular dysfunctions, such as, but not limited to nystagmus, strabismus, convergence insufficiency (CI), convergence excess, divergence insufficiency and divergence excess.

The head mounted display 110 can include circuitry disposed within a housing 150. The circuitry can include a right eye display 122, a left eye display 124, one or more right eye image capturing devices 126, one or more left eye image capturing devices 128, one or more right eye light emitting diodes 130, one or more left eye light emitting diodes 132, a right eye controller 134, a left eye controller 136, one or more display controllers 138, and one or more hardware interfaces 140.

The right and left eye displays 122 and 124 can be disposed within the housing 150 such that the right eye display 122 is positioned in front of the right eye of the user when the housing 150 is mounted on the user's head and the left eye display 124 is positioned in front of the left eye of the user when the housing 150 is mounted on the user's head. In this configuration, the right eye display 122 and the left eye display 124 can be controlled by the one or more display controllers 138 to render images on the right and left eye displays 122 and 124 to induce a stereoscopic effect, which can be used to generate three-dimensional images, where objects in the images can be perceived by the user's vision system as being at different depths while maintaining constant focal length between the user's right eye and the right eye display 122 and between the user's left eye and the left eye display 124. In exemplary embodiments, the right eye display 122 and/or the left eye display 124 can be implemented as a light emitting diode (LED) display, an organic light emitting diode (OLED) display (e.g., passive-matrix (PMOLED) display, active-matrix (AMOLED) display), and/or any suitable display.

The one or more right eye image capturing devices 126 can be disposed in the housing 150 relative to the right eye display 122 so that the one or more right eye image capturing devices 126 can be positioned and oriented to capture images of the user's right eye as the user views the right eye display 122. Likewise, the one or more left eye image capturing devices 128 can be disposed in the housing 150 relative to the left eye display 124 so that the one or more left eye image capturing devices 128 can be positioned and oriented to capture images of the user's left eye as the user views the left eye display 124. In exemplary embodiments, the one or more right and left eye image capturing devices 122 and 124 can be infrared (IR) cameras configured to have a particular sensitivity to IR light (e.g., to capture images of IR radiation).

The one or more right eye light emitting diodes 130 can be disposed in the housing 150 relative to the right eye display 122 and the one or more right eye light emitting diodes so that the one or more light emitting diodes 130 can be positioned and oriented to emit light towards the user's right eye as the user views the right eye display 122. Likewise, the one or more left eye light emitting diodes 132 can be disposed in the housing 150 relative to the left eye display 124 so that the one or more left eye light emitting diodes 132 can be positioned and oriented to emit light towards the user's left eye as the user views the left eye display 124. In exemplary embodiments, the one or more right and left eye light emitting diodes 130 and 132 can be infrared (IR) light emitting diodes configured to emit IR light. In some embodiments, the light emitting diodes project infrared light into the eye at about ten percent (10%) of the safety limit.

The right eye controller 134 can be operatively coupled to the one or more right eye image capturing devices 126 to control an operation of the one or more right eye image capturing devices 126 and/or to process the images of the right eye captured by the one or more right eye image capturing devices 126. Likewise, the left eye controller 136 can be operatively coupled to the one or more left eye image capturing devices 128 to control an operation of the one or more left eye image capturing devices 128 and/or to process the images of the left eye captured by the one or more left eye image capturing devices 128. As one non-limiting example, the right and left eye controllers 134 and 136 can be configured to control a shutter, aperture, refresh rate, discharge rate, and the like of the one or more right and left eye image capturing devices 122 and 124, respectively. As another non-limiting example, the right and left eye controllers 134 and 136 can monitor and/or track the movement of the user's right and right eyes as the user views the right and left eye displays 126, respectively, which can be utilized by exemplary embodiments to effect vision therapy of the user for binocular dysfunctions. While separate controllers in the form of the right and left eye controllers 134 and 136 are utilized to control and interface with the right and left eye image capturing device 122 and 124, exemplary embodiments of the present disclosure can be implemented with a single integrated controller to control and interface with the right and left eye image capturing devices 122 and 124.

In some embodiments, the right eye controller 134 and/or left eye controller 136 can be implemented with microcontrollers or microprocessors configured to detect eye motion using eye-tracking firmware/software. In some embodiments, the eye tracking system (e.g., including the image capturing devices and the right and left eye controls) is capable of real-time eye tracking of about 40 frames per second. The light emitting diodes (e.g., operating as IR light sources) illuminate each eye in a dark environment of the head mounted display.

While an illustrative embodiment of the head mounted display 110 is described herein as including components, such as the right and left image capturing devices 126 and 128, the right and left LEDs 130 and 132, and the right and left eye controllers 134 and 136, respectively, embodiments of the head mounted display may be devoid of one or more of these components. For example, in some embodiments, the head mounted display without eye tracking functionality may be devoid of these components. For such embodiments, the system 100 can utilize user feedback to facilitate measurement and assessment of oculomotor function.

The one or more display controllers 138 can be operatively coupled to right and left eye displays 122 and 124 to control an operation of the right and left eye displays 122 and 124 in response to input received from the computing system 170 and in response to positions of the user's right and left eyes as described herein. In exemplary embodiments, the one or more display controllers 138 can be configured to render images on the right and left eye displays of the same scene and/or objects, where images of the scene and/or objects are render at slightly different angles or points-of-view to facilitate the stereoscopic effect. In exemplary embodiments, the one or more display controllers 138 can include graphical processing units.

The one or more hardware interfaces 140 can facilitate communication between the head mounted display 110 and the computing system 170. The head mounted display 110 can be configured to transmit data to the computing system 170 and to receive data from the computing system 170 via the one or more hardware interfaces 140. As one example, the one or more hardware interfaces 140 can be configured to receive data from the computing system 170 corresponding to images and can be configured to transmit the data to the one or more display controllers 138, which can render the images on the right and left eye displays 122 and 124 to provide a virtual reality environment in three-dimensions (e.g., as a result of the stereoscopic effect) that is designed to facilitate assessment of oculomotor function. Likewise, the one or more hardware interfaces 140 can receive data from the right and left eye controllers 134 and 136 corresponding to right and left eye positions or angles of the user, respectively, and can transmit the data to the computing system 170, which can use the data to control an operation of oculomotor assessment software platform (OASP) 172 to facilitate oculomotor assessment (e.g., by tracking or recording the convergence and divergence of a user's eyes in response to stimuli in the virtual reality environment).

The housing 150 can include a mounting structure 152 and a display structure 154. The mounting structure 152 allows a user to wear the head mounted display 110 on his/her head and to position the display structure over his/her eyes to facilitate viewing of the right and left eye displays 122 and 124 by the right and left eyes of the user, respectively. The mounting structure can be configured to generally mount the head mounted display 110 on a user's head in a secure and stable manner. As such, the head mounted display 110 generally remains fixed with respect to the user's head such that when the user moves his/her head left, right, up, and down, the head mounted display 110 generally moves with the user's head.

Figure 3:
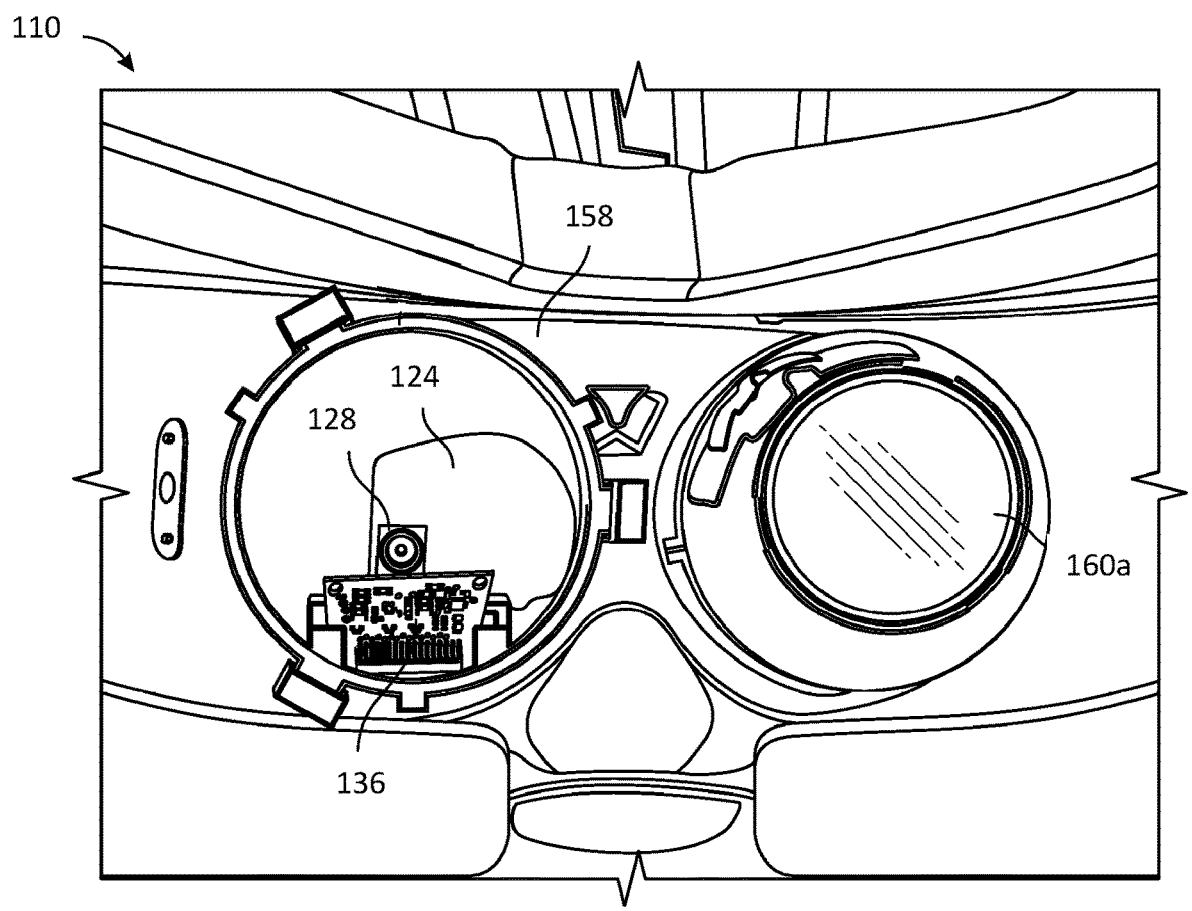
FIG. 3 depicts a portion of an embodiment of a head mounted display with a left lens removed to reveal a left eye portal, a left eye display, an embodiment of a mechanical fixture with a left eye controller, and the image capturing device, where the right eye side includes a lens mounted over a right eye portal.

Referring to FIGS. 1 and 3, the display structure 154 can be contoured to fit snug against a user's face to cover the user's eyes and to generally prevent light from the environment surrounding the user from reaching the user's eyes. The display structure 154 can include a right eye portal 156 and a left eye portal 158 formed therein. A right eye lens 160a can be disposed over the right eye portal and a left eye lens 160b can be disposed over the left eye portal. The right eye display 122, the one or more right eye image capturing devices 126, and the one or more right eye light emitting diodes 130 can be disposed within the display structure 154 behind the lens 160 covering the right eye portal 156 such that the lens 156 is disposed between the user's right eye and each of the right eye display 122, the one or more right eye image capturing devices 126, and the one or more right eye light emitting diodes 130. The left eye display 124, the one or more left eye image capturing devices 128, and the one or more left eye light emitting diodes 132 can be disposed within the display structure 154 behind the lens 160 covering the left eye portal 158 such that the lens 160 is disposed between the user's left eye and each of the left eye display 124, the one or more left eye image capturing devices 128, and the one or more left eye light emitting diodes 132.

While the one or more right eye image capturing devices 126 and the one or more right eye light emitting diodes 130 are described as being disposed behind the lens 160 covering the right eye portal as an example embodiment, in exemplary embodiments of the present disclosure the one or more right eye image capturing devices 126 and/or the one or more right eye light emitting diodes 130 can be disposed in front of and/or around the lens 160 covering the right eye portal such that lens 160 is not positioned between the user's right eye and the one or more right eye image capturing devices 126 and/or the one or more right eye light emitting diodes 130. Likewise, while the one or more left eye image capturing devices 128 and the one or more left eye light emitting diodes 132 are described as being disposed behind the lens 160 covering the left eye portal as an example embodiment, in exemplary embodiments of the present disclosure the one or more left eye image capturing devices 128 and/or the one or more left eye light emitting diodes 132 can be disposed in front of and/or around the lens 160 covering the left eye portal such that lens 160 is not positioned between the user's left eye and the one or more right eye image capturing devices 126 and/or the one or more right eye light emitting diodes 130.

Figure 4:
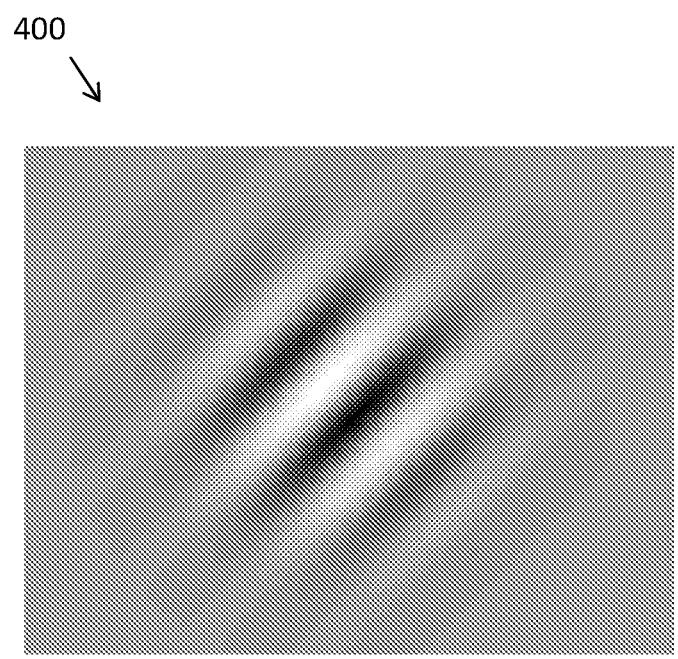
FIG. 4 shows an example using a difference of Gaussian to reduce accommodative stimulation.

The computing system 170 can be configured to execute the OASP 172 to generate objects/stimuli in a virtual reality environment to assess oculomotor function via the head mounted display 110. Execution of the OASP 172 by the computing device can cause the head mounted display to render images that include objects on which a user typically cannot focus clearly. The objects/stimuli can be formed using one or more techniques to reduce stimulation of accommodation system or the blur input. For example, the objects/stimuli can be formed using the Gabor patch, small letters, and/or any other techniques that reduce stimulation of accommodation and/or blur. The Gabor patch uses a series of differences of Gaussians (DOG) stimuli which appear as blurry lines, such as those shown in the exemplary Gabor patch 400 of FIG. 4. The visual system cannot focus on objects that are formed with the Gabor patch; hence the accommodative system is minimally stimulated by exemplary embodiments of the present disclosure.

The computing system 170 can execute the OASP 172 to dynamically adjust the objects/stimuli to measure a response of the user's eyes as the user attempts to aim his/her eyes at the objects/stimuli. The head mounted display 110 can be used to track and/or monitor a position of the of the user's eyes relative to an expected and/or desired position of the user's eyes to capture vergence parameters which can be output to the computing system 170 (and transmitted from the computing system to a remote computing system) to facilitate quantitative and/or qualitative assessment by a clinician.

To facilitate assessment of oculomotor function, the computing system 170 executes the OASP 172 to transmit data to the head mounted display 110 including right and left images to be rendered by the right and left eye displays 122 and 124. In response to rendering the right and left images, the user's visual system can perceive the right and left images as a single image in three-dimensional space (e.g., using the stereoscopic effect). The right and left images rendered on the right and left eye displays 122 and 124, respectively, can be offset from each other so that to fuse some objects/stimuli, the visual system must converge more than other objects. The more converged the eyes, the closer a visual object will be perceived to the person within a head mounted display. The position and/or angle of the user's eyes can be adjusted based on the objects included in the right and left images and the one or more right and left image capturing devices 126 and 128, respectively, can track the position and/or angle of the user's eye, which can be transmitted to the computing system 170. The computing system can receive the position and/or angle of the user's eyes as inputs in response to the right and left images being displayed. For example, the position of the right and left eye of the user can be tracked to determine a point in three-dimensional virtual reality space at which the user's eyes are fused. Based on the monitored or tracked eye position and/or angle, the computing system 170, executing the OASP, can generate subsequent right and left images to assess oculomotor function of the user's eyes.

Some examples of visual stimuli that can be incorporated into the right and left images can create animations of objects/stimuli in three-dimensions, where the animations of the objects/stimuli includes, for example, step, ramp, combinational step and ramp, sinusoidal, double step or open loop stimuli.

While an example embodiment has been illustrated including a head mounted display 110 and a computing system 170, exemplary embodiments of the present disclosure can be configured such that the head mounted display includes the computing system 170 and/or is configured to perform the functions and operations of the computing system 170 such that the head mount display 110 is a self-contained, stand-alone device that provides for oculomotor assessment as described herein.

Figure 2:
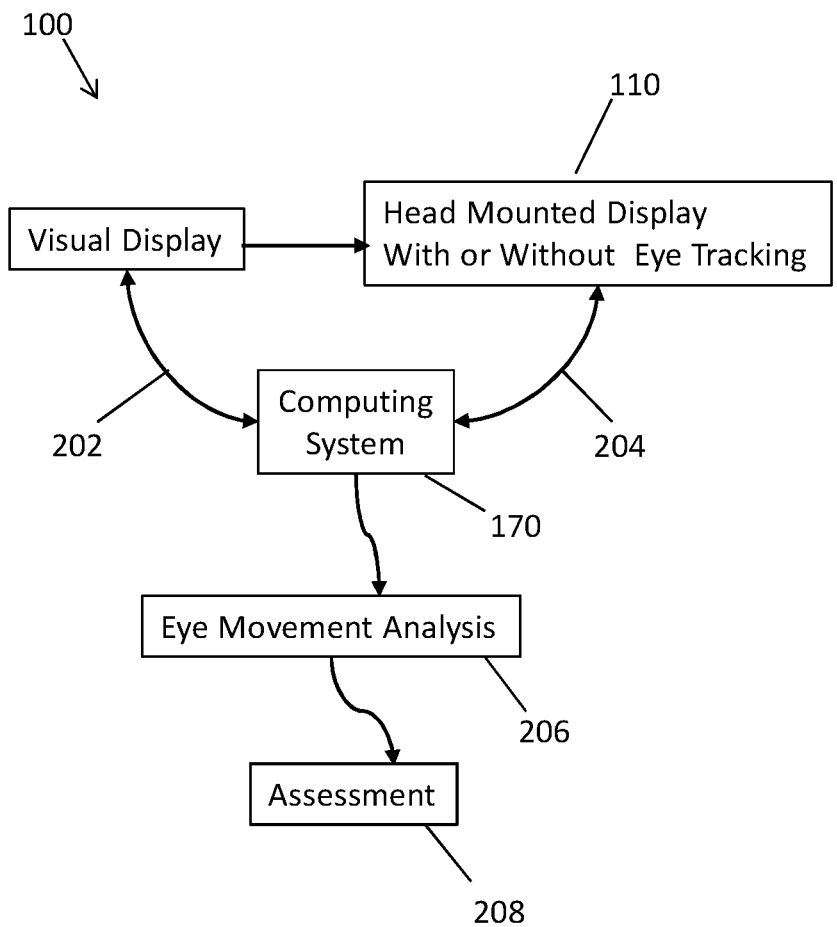
FIG. 2 depicts a functional diagram of the exemplary oculomotor assessment system in accordance with exemplary embodiments of the present disclosure.

Referring to FIGS. 1-2, in an exemplary operation, the system 100 can obtain oculomotor measurements and generate oculomotor assessments. While examples of optometric measurements and assessments are described for illustrative embodiments of the system 100, other optometric measurements can be obtained by exemplary embodiments of the system 100. The computing system 170 can execute the OASP interface with the head-mounted display 110 to render visual display 202 of one or objects in the virtual reality environment to appear in three-dimensional space having a three-axis virtual coordinate system. The computing system 170 via execution of the OASP can control an operation of the head-mounted display 110 to change how the objects/stimuli are rendered in the three-dimensional space. The computing system 170 can receive feedback 204 from the head mounted display 110, e.g., via the eye tracking components, to measure and analyze eye movements 206 via the OASP, and to generate an assessment 208 of the oculomotor function of a user of the system 100.

The computing system 170 can execute the OASP 172 to render an object/stimuli via in a virtual reality environment via the head mounted display 110 to objectively measure and determine near point of convergence and then objectively measure dissociated and associated phoria and fixation disparity. For example, the object/stimuli can be rendered on the right and/or left eye displays at a virtual distance from the user (i.e. the object/stimuli can be rendered to appear a specified distance away from the user, while the focal distance between the user's eyes and the right and left eye displays remain fixed). The user's eyes can converge on the object/stimuli and the object/stimuli can be rendered as an animation where the object/stimuli appear to move towards the user until the user's eyes can no longer converge on the object/stimuli. Eye tracking will record the angular position of the eye which will both rotate inward until one eye does not substantially move inward any longer. When the limit of binocular fusion is attained this will be the vergence angular demand that is closest to the user and be assessed as the user's near point of convergence. The user can also report via pushing a button or verbal feedback when the object/stimuli appears double and the vergence angular demand of the last visual stimuli will be the user's near point of convergence. The computing system 170 can measure (dissociated and associated) phoria while constantly rendering animated objects/stimuli to one eye at a time, occluding visual stimuli to the other eye, except for occasional flashing of rendering animated objects/stimuli. The computing system 170 can execute the OASP 172 to measure the steady state error (fixation disparity) while constantly rendering animated objects/stimuli via the head mounted display 110 and measuring the difference between where the location of the eyes is presently located and the target. The exponential decay and final resting spot of the occluded eye can be tracked and recorded by the computing system 170 based on tracking of eye movement by the head mounted display 110 and can be recorded through user feedback, if on a device without eye tracking (e.g., via a keyboard, mouse, joystick, microphone, etc., operatively coupled to the computing system 170).

The computing system 170 can execute the OASP 172 to measure saccades (horizontal and vertical) and smooth pursuit. The computing system 170 can measure saccades by measuring binocular coordination while rendering animated objects/stimuli that stimulate vertical and/or horizontal saccadic eye movements. The computing system 170 can similarly measure smooth pursuit by measuring binocular coordination while rendering animated objects/stimuli that makes smoothly moving stimuli stimulated via a ramp or sinusoidal function. Saccadic movements can be side to side or up to down rapid eye movements or stimulated on an oblique angle. Saccadic movement are rapid open loop eye movements to project the object of interest to the fovea (highest density of photoreceptors in the retina) by abruptly changing gaze from one location to another stimulating conjugate eye movement. Smooth pursuit movements are classified as feedback-controlled rotation of the eyes to follow a target smoothly moving using conjugate eye movements. The ability for the eyes to track and identify objects, the velocity at which they do, the accuracy and precision of eye movement responses to visual stimuli, and the number of tracking in a given time can also be either assessed and recorded by the computing system 170 based on tracking of eye movement by the head mounted display 110 and can be recorded through user feedback, if on a device without eye tracking (e.g., via a keyboard, mouse, joystick, microphone, etc., operatively coupled to the computing system 170).

The computing system 170 can execute the OASP 172 to assess oculomotor/binocular endurance and adaptation. The computing system 170 can assess oculomotor/binocular endurance by measuring degradation in the binocular system while rendering multiple animated objects/stimuli that create a visually demanding experience for the user. The ability for the eyes to track and identify objects, the change in velocity from the beginning of the assessment to the end of the assessment, the change in movement positional magnitude from the beginning of the assessment to the end of the assessment, and the change in accuracy/precision of the eye movements in relation to the objects/stimuli can be tracked and recorded by the computing system 170 based on tracking of eye movement by the head mounted display 110 and can be recorded through user feedback, if on a device without eye tracking (e.g., via a keyboard, mouse, joystick, microphone, etc., operatively coupled to the computing system 170). The computing system 170 can adapt any of the oculomotor systems using positive or negative gain protocols including by not limited to intermixing large and small visual step stimuli, slow and fast ramp stimuli, open loop gain visual stimuli, double and single step visual stimuli. The change in response amplitude, peak velocity, error, accuracy and precision as a function of time will be assessed within computing system 170 or recorded through user feedback, if on a device without eye tracking (e.g., via a keyboard, mouse, joystick, microphone, etc., operatively coupled to the computing system 170).

The computing system 170 can execute the OASP to objectively measure fusional range and vergence facility. The vergence facility can be measured where the object/stimuli rendered by the head mounted display 110 for the right and/or left eyes moves inward or outward, analogous to a flipper prism. The ability of the eyes to adjust to the change in the object/stimuli, either quantified objectively by tracking the user's eye movements or through user feedback (e.g., via a keyboard, mouse, joystick, microphone, etc., operatively coupled to the computing system 170), can be recorded by the system 100. The number of vergence responses that a user can perform within a given specific time will be recorded by system 100. The fusional range, both positive and negative ranges, can be measured where the object/stimuli rendered by the head mounted display 110 for the right and/or left eyes moves inward (positive) or outward (negative), analogous to prism bar. The ability of the eyes to adjust to the change in the object/stimuli, either quantified objectively by tracking the user's eye movements or through user feedback (e.g., via a keyboard, mouse, joystick, microphone, etc., operatively coupled to the computing system 170), can be recorded by the system 100.

The computing system can execute the OASP 172 to objectively measure eye movement parameters including, but not limited to the following: vergence peak velocity, accuracy, response amplitude, latency, time to peak velocity, time constant, error, variance, asymmetry between left and right eye movement, magnitude height and width of fusion initiating component, and/or measure ratio of convergence to divergence peak velocity at different initial vergence angles. The computing system 170 can objectively measure the peak velocity of an abruptly changing visual stimulus along midline, a vergence step stimulus also called a jump duction. The derivative of the change in eye position can be calculated and saved as vergence peak step velocity. The initial response amplitude can also be measured. The vergence stimuli presented can also include a ramp or sinusoid to assess the vergence system ability to track smoothly changing targets. Stimuli that abruptly change and then are visually extinguished can be used to assess the preprogrammed fusion initiating component of vergence. The computing device 170 can execute the OASP 172 to measure binocular coordination by rending objects/stimuli in the virtual environment by the head mounted display to cause the user to make multi-directional eye movements. The ability for the user's eyes to track and identify objects, the velocity at which they do, and the precision/accuracy can be tracked by the system 100 or can be recorded through user feedback, if on a device without eye tracking (e.g., via a keyboard, mouse, joystick, microphone, etc., operatively coupled to the computing system 170).

The objective oculomotor measurements measured by the system 100 can be combined into a weighted assessment that suggests whether a person is within normal ranges or should seek an eye care professional assessment. The weighted assessment can be a combination of any of the aforementioned parameters/characteristics. One embodiment of the weighted assessment can the magnitude of change of an oculomotor characteristic/parameter ($\Delta$OculomotorParameter (i)) divided by the time constant (time constant (i)) as a function of time bin (e.g., i=1 to i=N). For example, the time constant can represent an amount of time it takes for the eye movement of a user to change by a specified amount (e.g., 66.7%) of a total change in the eye movement characteristic/parameter. The time bin can correspond to a number of iterations performed for the oculomotor parameter(s) and/or a discreet time interval for the oculomotor parameters. These weighted assessments can be used to create different indices corresponding to various binocular disorders. An embodiment of the equation can be described below where the assessment would be the summation from the first parameter (i) to the last parameter (N) of the weight multiplied by the change oculomotor parameter divided by the time constant plus the scalar oculomotor parameter (Oculomotor Parameter (i)), which represented a baseline value of the oculomotor parameter independent of time.

$$\text{Assessment} = \sum_{i=1}^{i=N} \text{Weight}\left[\frac{\Delta OculomotorParameter(i)}{\text{time constant}(i)} + \text{Oculomotor Parameter}(i)\right]$$

The system 100 can generate quantitative data, which can be used by clinicians to quantitatively assess a patient's visual system and can be used to assess progression or changes from therapeutic interventions.

The OASP 172 can utilize one or more trained machine learning algorithms to facilitate the objective assessment of oculomotor function of users. One or more machine learning algorithms can be trained using a corpus of training data associated with measured oculomotor characteristics and oculomotor assessments or diagnoses to generate one or machine learning models. The trained machine learning models can be incorporated into the OASP 172 to facilitate objective assessment of oculomotor function. As one example, an embodiment of the OASP 172 can use a neural network or machine learning algorithm to assess the objective near point of convergence, positive and negative fusional range, dissociated and associated phoria, fixation disparity, vergence peak velocity, ratio of vergence peak velocity divided by the response amplitude, quality and number of saccadic eye movements, smooth pursuit eye movements, vergence facility, asymmetry between the left and right eye, accuracy, variance, blink rate, convergence to divergence peak velocity ratio, binocular endurance and eye movement adaptation. Using a weight of these parameters, the OASP can determine whether the subject should see a professional eye care provider. Through the use of neural networks or machine learning, the OASP 172 can independently change the rendering of the objects/stimuli to reduce the duration of an assessment while still maintaining sensitivity and specific of the assessment. The use of a neural network or machine learning algorithm can change the program sequence to become non-linear in assessment such as fusional range or near point of convergence when a user is doing well in the assessment to reduce the assessment duration of time. Another example of the use of a neural network or machine learning algorithm can be the change in difficulty of visually demanding task in oculomotor/binocular endurance assessment. The computing system 170 can execute the OASP 172 to implement the machine learning models to dynamically adjust which oculomotor characteristics are measured for a user based on how the user's visual system responds to the stimuli for measuring the oculomotor characteristics. In this manner, embodiments of the system 100 can render different stimulus and different measurements for different patients while still providing accurate assessment of the users' oculomotor function, which can reduce the amount of resources required to assess some users and/or can reduce the amount of time required to assess some users.

As one non-limiting example, embodiments of the system 100 can use support vectors trained using supervised learning. In other non-limiting examples, the machine learning algorithm(s) used by the system can include, for example, supervised learning algorithms, unsupervised learning algorithm, artificial neural network algorithms, association rule learning algorithms, hierarchical clustering algorithms, cluster analysis algorithms, outlier detection algorithms, semi-supervised learning algorithms, reinforcement learning algorithms and/or deep learning algorithms Examples of supervised learning algorithms can include, for example, AODE; Artificial neural network, such as Backpropagation, Autoencoders, Hopfield networks, Boltzmann machines, Restricted Boltzmann Machines, and/or Spiking neural networks; Bayesian statistics, such as Bayesian network and/or Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor algorithms and/or Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and/or Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, and/or Support vector machines; Quadratic classifiers; k-nearest neighbor; Boosting; Decision trees, such as C4.5, Random forests, ID3, CART, SLIQ, and/or SPRINT; Bayesian networks, such as Naive Bayes; and/or Hidden Markov models. Examples of unsupervised learning algorithms can include Expectation-maximization algorithm; Vector Quantization; Generative topographic map; and/or Information bottleneck method. Examples of artificial neural network can include Self-organizing maps. Examples of association rule learning algorithms can include Apriori algorithm; Eclat algorithm; and/or FP-growth algorithm. Examples of hierarchical clustering can include Single-linkage clustering and/or Conceptual clustering. Examples of cluster analysis can include K-means algorithm; Fuzzy clustering; DBSCAN; and/or OPTICS algorithm. Examples of outlier detection can include Local Outlier Factors. Examples of semi-supervised learning algorithms can include Generative models; Low-density separation; Graph-based methods; and/or Co-training. Examples of reinforcement learning algorithms can include Temporal difference learning; Q-learning; Learning Automata; and/or SARSA. Examples of deep learning algorithms can include Deep belief networks; Deep Boltzmann machines; Deep Convolutional neural networks; Deep Recurrent neural networks; and/or Hierarchical temporal memory.

The visual stimulus render can be used to stimulate the disparity vergence system and minimize/control cues to the accommodative or proximal vergence. As one example, the objects/stimuli rendered can include, but are not limited to the Gabor patch, which uses a series of Difference of Gaussian (DoG) stimuli and appear as blurry lines, such as those shown in the exemplary Gabor patch of FIG. 4. The visual system cannot focus on objects that are formed with the Gabor patch; hence the accommodative system is minimally stimulated by exemplary embodiments of the present disclosure, which can be important for successful assessment of the disparity vergence system. Another non-limiting example of objects that can be rendered by exemplary embodiments of the present disclosure can include small letters, which a person focuses on clearly.

Figure 5:
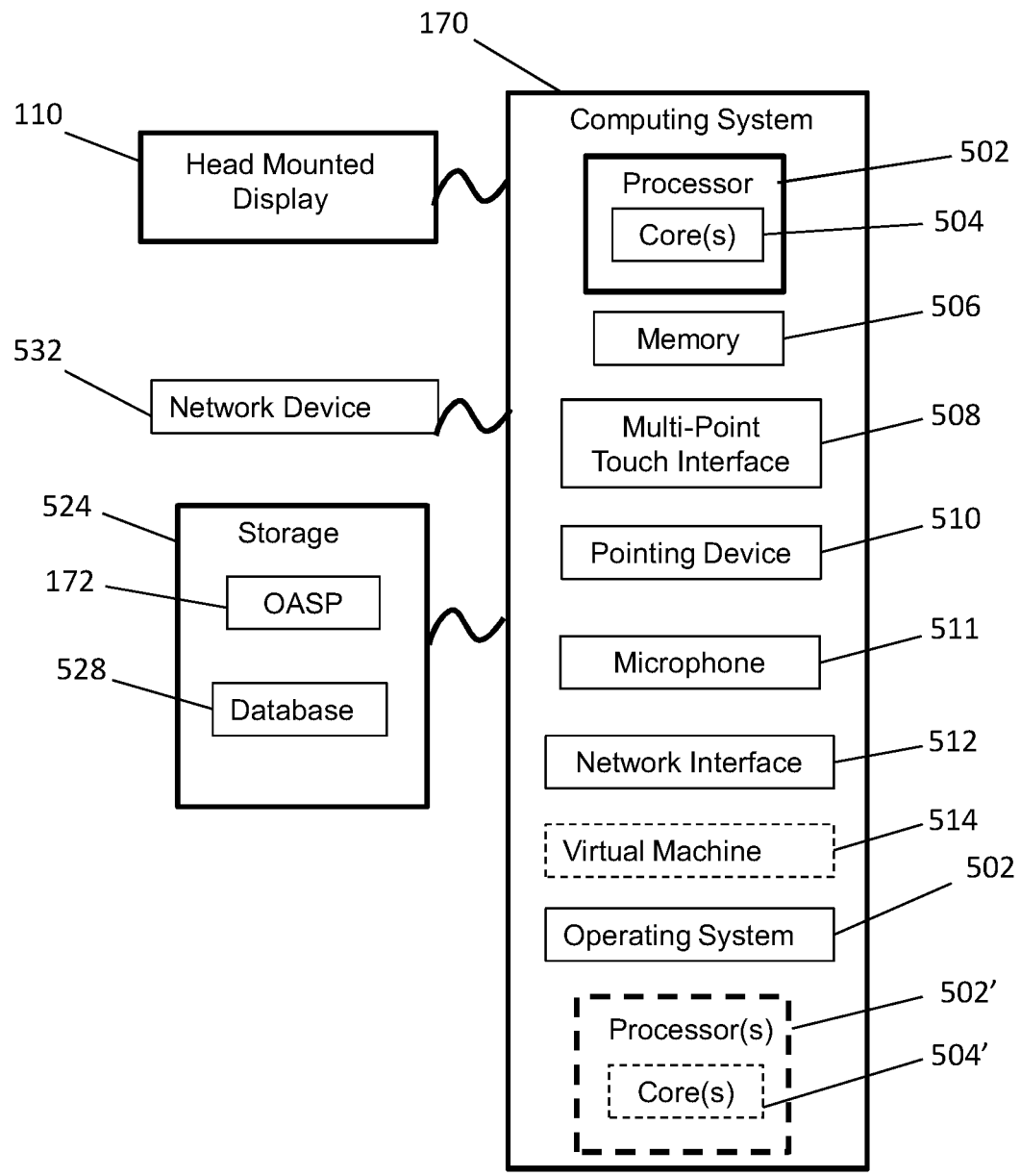
FIG. 5 is a block diagram of an exemplary embodiment of the computing system shown in FIG. 1.

FIG. 5 is a block diagram of an exemplary embodiment of the computing system 170. In some embodiments, the computing system 170 can execute virtual reality environment to be rendered through embodiments of the head mounted display 110. The computing system 170 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 506 included in the computing system 170 may store computer-readable and computer-executable instructions or software for implementing exemplary embodiments. The computing system 170 also includes processor 502 and associated core 504, and optionally, one or more additional processor(s) 502' and associated core(s) 504' (for example, in the case of computer systems having multiple processors/cores), for executing computer-readable and computer-executable instructions or software stored in the memory 506 and other programs for controlling system hardware. Processor 502 and processor(s) 502' may each be a single core processor or multiple core (504 and 504') processor and may be central processing units, graphical processing units, and the like.

Virtualization may be employed in the computing system 170 so that infrastructure and resources in the computing device may be shared dynamically. A virtual machine 514 may be provided to handle a process running on multiple processors so that the process appears to be using only one computing resource rather than multiple computing resources. Multiple virtual machines may also be used with one processor.

Memory 506 may include a computer system memory or random access memory, such as DRAM, SRAM, EDO RAM, and the like. Memory 506 may include other types of memory as well, or combinations thereof.

A user may interact with the computing system 170 through an embodiment of the head mounted display 510, which can display one or more objects in a virtual reality environment of the OASP executed by the computing system 170 in accordance with exemplary embodiments. The computing system 170 may include other I/O devices for receiving input from a user, for example, a keyboard or any suitable multi-point touch interface 508, a pointing device 510 (e.g., a mouse or joystick), a microphone 511, and the like. The computing device 170 may include other suitable conventional I/O peripherals.

The computing system 170 may also include one or more storage devices 524, such as a hard-drive, CD-ROM, or other computer readable media, for storing data and computer-readable instructions and/or software, such as the OASP 172 that implement exemplary embodiments of one or more virtual reality environments to facilitate assessment of oculomotor function and/or visual therapy for binocular dysfunctions. Exemplary storage device 524 may also store one or more databases for storing any suitable information required to implement exemplary embodiments. For example, exemplary storage device 524 can store one or more databases 528 for storing information, such as oculomotor measurements, oculomotor assessments, user data, user milestones, and the like. The databases may be updated at any suitable time to add, delete, and/or update one or more items in the databases.

The computing system 170 can include a network interface 512 configured to interface via one or more network devices 522 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 512 may include a built-in network adapter, network interface card, PCMCIA network card, card bus network adapter, wireless network adapter, USB network adapter, modem or any other device suitable for interfacing the computing system 170 to any type of network capable of communication and performing the operations described herein. Moreover, the computing system 170 may be any computer system, such as a workstation, desktop computer, server, laptop, handheld computer, tablet computer (e.g., the iPad™ tablet computer), mobile computing or communication device (e.g., the iPhone™ communication device), or other form of computing or telecommunications device that is capable of communication and that has sufficient processor power and memory capacity to perform the operations described herein.

The computing system 170 may run any operating system 516, such as any of the versions of the Microsoft® Windows® operating systems, the different releases of the Unix and Linux operating systems, any version of the MacOS® for Macintosh computers, any embedded operating system, Microsoft® Xbox operating systems for Xbox gaming systems, Playstation operating systems for PlayStation gaming systems, Wii operating systems for Wii gaming systems, any real-time operating system, any open source operating system, any proprietary operating system, or any other operating system capable of running on the computing device and performing the operations described herein. In exemplary embodiments, the operating system 516 may be run in native mode or emulated mode. In an exemplary embodiment, the operating system 516 may be run on one or more cloud machine instances.

Figure 6:
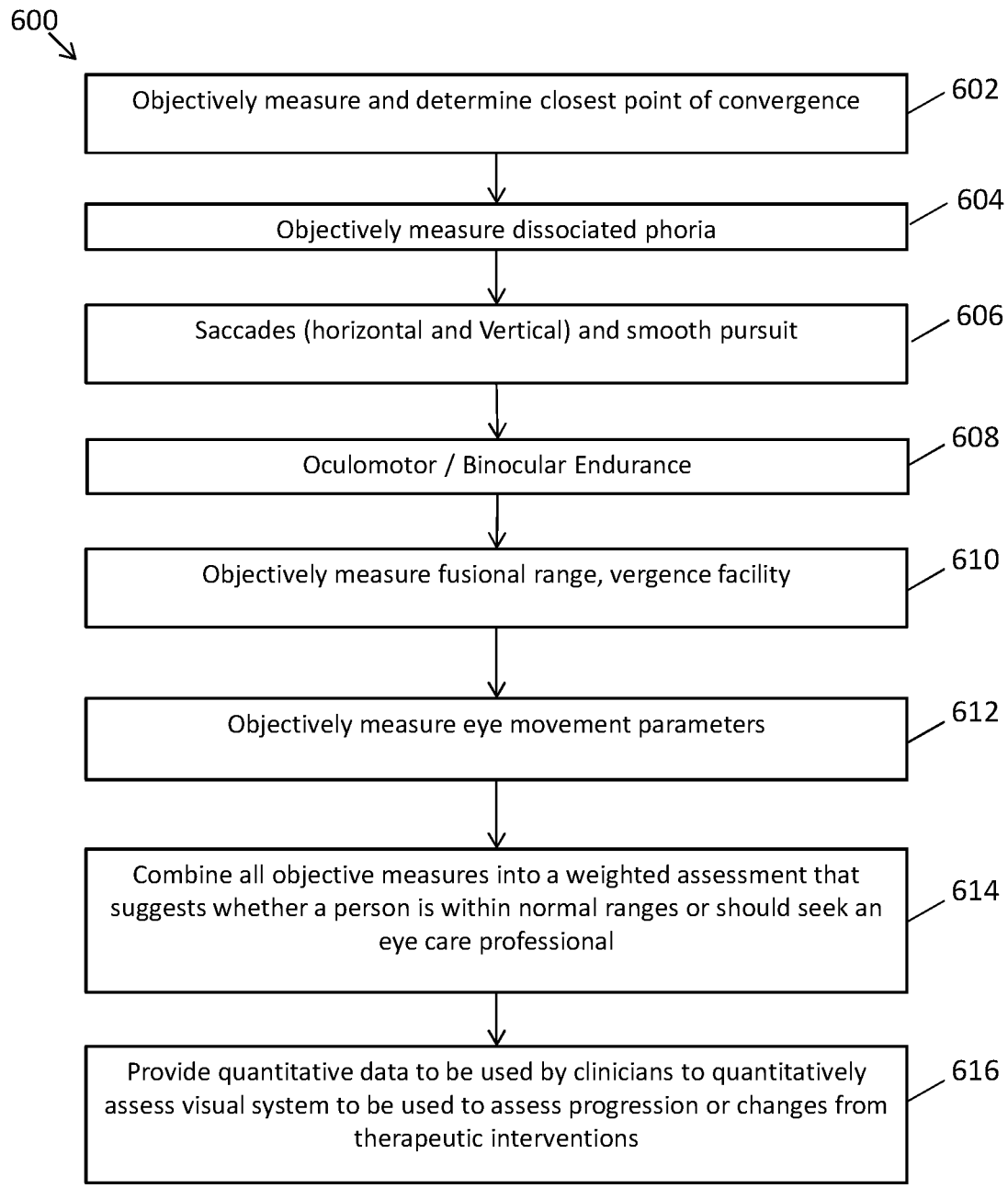
FIG. 6 is a flowchart illustrating an exemplary process for providing objective measurements for assessment and/or diagnosis for binocular dysfunction, in accordance with embodiments of the present disclosure.

FIG. 6 is a flowchart illustrating a process 600 for objectively assessing oculomotor function and/or binocular dysfunction via embodiments of the system 100. At step 602, the computing system executes the OASP to interact with the head mounted display to objectively measure and determine the near point of convergence, and at step 604 the computing system executes the OASP to interact with the head mounted display to objectively measure dissociated and associated phoria and fixation disparity. At step 606, the computing system executes the OASP to interact with the head mounted display to measure saccades (horizontal and vertical) and smooth pursuit, and at step 608, the computing system executes the OASP to interact with the head mounted display to assess oculomotor/binocular endurance and oculomotor adaptation. At step 610, the computing system executes the OASP to interact with the head mounted display to objectively measure fusional range and vergence facility of a visual system of a user. At step 612, the computing system executes the OASP to interact with the head mounted display to objectively measure eye movement parameters, such as, but not limited to vergence peak velocity, accuracy, response amplitude, latency, time to peak velocity, time constant, error, variance, asymmetry between left and right eye movement, ramp response speed, dissection of movement to assess magnitude height and width of fusion initiating component, measure ratio of convergence to divergence peak velocity at different initial vergence angles.

At step 614, the objective measures are combined by the computing system executing the OASP into a weighted assessment that suggests whether a person is within normal ranges or should seek an eye care professional. At step 616, the computing system executes the OASP to provide quantitative data, which can be used by clinicians to quantitatively assess the visual system to be used to assess progression or changes from therapeutic interventions.

Figure 7:
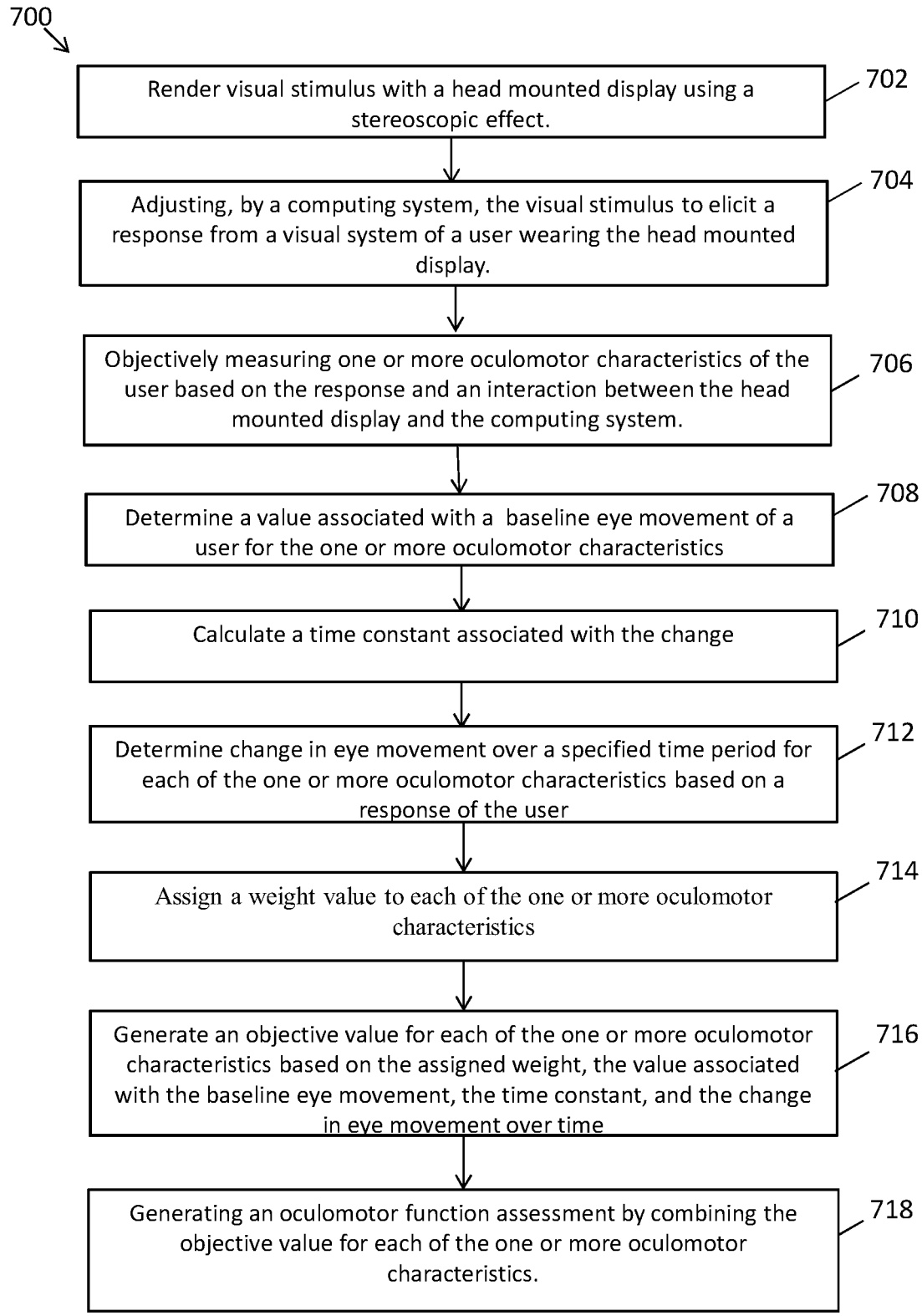
FIG. 7 is a flowchart illustrating another exemplary process for providing objective measurements for assessment and/or diagnosis for oculomotor function in accordance with embodiments of the present disclosure.

FIG. 7 is a flowchart illustrating another exemplary process 700 for providing objective measurements for assessment and/or diagnosis for oculomotor function in accordance with embodiments of the present disclosure. At step 702, a visual stimulus is rendered with a display (e.g., head mounted display 110) using the stereoscopic effect. At step 704, the visual stimulus is adjusted by the computing system to elicit a response from a visual system of the user viewing the display. At step 706, one or more oculomotor characteristics are measured by the system based on the response and interaction between the display and computing system. At step 708, a baseline value associated with the eye movement of the user for each of the oculomotor characteristics is determined, and at step 710, a change in eye movement over a specified time period for each of the one or more oculomotor characteristics is determined based on a response of the user. At step 712, a time constant associated with the change is calculated, and at step 714, a weight value is assigned to each of the one or more oculomotor characteristics. At step 716, an object value is generated for each of the oculomotor characteristics based on the assigned weight, the time constant, and the change in eye movement over time, and at step 718, the object value for each of the oculomotor characteristics is combined to generate an oculomotor function assessment. In one example, the objective value for each of the oculomotor characteristics can be summed to generate the oculomotor function assessment, which can be used by clinicians to quantitatively assess a patient's visual system and can be used to assess progression or changes from therapeutic interventions.

Figure 8:
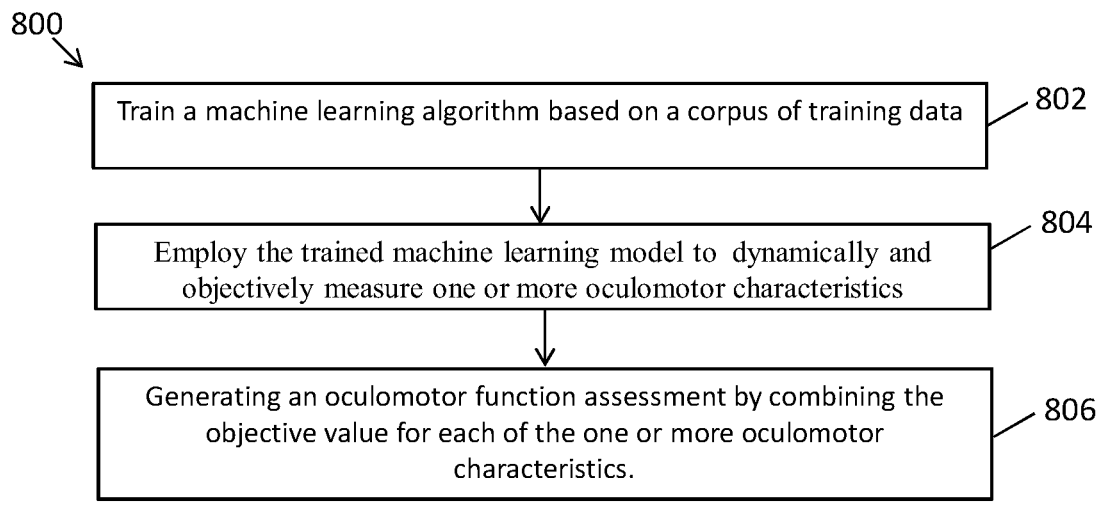
FIG. 8 is a flowchart illustrating an exemplary process for dynamic and objective assessment of oculomotor function based on a trained machine learning model in accordance with embodiments of the present disclosure.

FIG. 8 is a flowchart illustrating an exemplary process 800 for dynamic and objective assessment of oculomotor function in accordance with embodiments of the present disclosure. At step 802, a machine learning algorithm can be trained using a corpus of training data associated with measured oculomotor characteristics and oculomotor assessments or diagnoses to generate one or machine learning models. At step 804, the trained machine learning model is employed by the computing system to dynamically and objectively measure one or more oculomotor characteristics via the head mounted display. At step 806, an oculomotor function assessment is generated by combining the objective value for each of the one or more oculomotor characteristics.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The foregoing description of the specific embodiments of the subject matter disclosed herein has been presented for purposes of illustration and description and is not intended to limit the scope of the subject matter set forth herein. It is fully contemplated that other various embodiments, modifications and applications will become apparent to those of ordinary skill in the art from the foregoing description and accompanying drawings. Thus, such other embodiments, modifications, and applications are intended to fall within the scope of the following appended claims. Further, those of ordinary skill in the art will appreciate that the embodiments, modifications, and applications that have been described herein are in the context of particular environment, and the subject matter set forth herein is not limited thereto, but can be beneficially applied in any number of other manners, environments and purposes. Accordingly, the claims set forth below should be construed in view of the full breadth and spirit of the novel features and techniques as disclosed herein.

What is claimed is:

1. A system for performing an assessment of oculomotor function of a user, the system comprising:
a head mounted display configured to generate a stereoscopic effect viewable by the user;
a computing system in communication with the head mounted display, the computing system comprising:
a memory storing computer readable instructions; and
a processing device for executing the computer readable instructions, the computer readable instructions controlling the processing device to perform operations comprising:
rendering visual stimulus with the head mounted display;
adjusting the visual stimulus to elicit a response from a visual system of the user;
objectively measuring at least a subset of a plurality of oculomotor characteristics of the user based on the response;
based on the objective measurement of the at least the subset of the plurality of oculomotor characteristics of the user, dynamically adjusting the rendering of the visual stimulus to a non-linear program sequence, using a trained machine learning model, to reduce at least one of a duration of an oculomotor function assessment and resources required to complete the oculomotor function assessment; and
generating the oculomotor function assessment by combining the at least the subset of the plurality of oculomotor characteristics;
wherein the dynamic adjustment of the rendering of the visual stimulus using the trained machine learning model does not reduce the sensitivity of the oculomotor function assessment despite the reduced assessment duration and/or the resources required to complete the oculomotor function assessment.

2. The system of claim 1, wherein the head mounted display is configured to measure movement of the user's eyes and transmit the measure of movement to the computing system.

3. The system of claim 2, wherein adjusting the visual stimulus is based on the measure of eye movement.

4. The system of claim 2, wherein objectively measuring the at least the subset of the plurality of oculomotor characteristics is based on the measure of eye movement.

5. The system of claim 1, wherein the plurality of oculomotor characteristics includes at least one of a near point of convergence, dissociated and associated phoria, fixation disparity saccades, smooth pursuit, binocular endurance, eye movement adaptation, fusional range, or vergence facility.

6. The system of claim 1, wherein the plurality of oculomotor characteristics include at least one of vergence peak velocity, accuracy, response amplitude, latency, time to peak velocity, time constant, error, variance, asymmetry between left and right eye movement, ramp respond speed, dissection of eye movement to assess magnitude height and width of fusion initiating component, or measure ratio of convergence to divergence peak velocity at different initial vergence angles.

7. The system of claim 1, wherein the plurality of oculomotor characteristics is weighted.

8. The system of claim 1, wherein the trained machine learning model is a first trained machine learning model, wherein a second trained machine learning module is used to render the visual stimulus with the head mounted display or to adjust the visual stimulus to elicit the response from the visual system of the user.

9. A method for performing an assessment of oculomotor function of a user, the method comprising:
rendering visual stimulus with a head mounted display using a stereoscopic effect;
adjusting, by a computing system, the visual stimulus to elicit a response from a visual system of the user wearing the head mounted display;
objectively measuring at least a subset of a plurality of oculomotor characteristics of the user based at least on the response;
based on the objective measurement of the at least the subset of the plurality of oculomotor characteristics of the user, dynamically adjusting the rendering of the visual stimulus to a non-linear program sequence, using a trained machine learning model, to reduce at least one of a duration of an oculomotor function assessment and resources required to complete the oculomotor function assessment; and
generating the oculomotor function assessment by combining the at least the subset of the plurality of oculomotor characteristics;
wherein the dynamic adjustment of the rendering of the visual stimulus using the trained machine learning model does not reduce the sensitivity of the oculomotor function assessment despite the reduced assessment duration and/or the resources required to complete the oculomotor function assessment.

10. The method of claim 9, further comprising:
measuring movement of the user's eyes via the head mounted display; and
transmitting a measure of movement of the user's eyes to the computing system.

11. The method of claim 10, wherein adjusting the visual stimulus is based on the measure of movement.

12. The method of claim 10, wherein objectively measuring the at least the subset of the plurality of oculomotor characteristics is based on the measure of movement.

13. The method of claim 9, wherein the plurality of oculomotor characteristics includes at least one of a near point of convergence, dissociated and associated phoria, fixation disparity, saccades, smooth pursuit, binocular endurance, eye movement adaptation, fusional range, or vergence facility.

14. The method of claim 9, wherein the plurality of oculomotor characteristics include at least one of vergence peak velocity, accuracy, response amplitude, latency, time to peak velocity, time constant, error, variance, asymmetry between left and right eye movement, ramp respond speed, dissection of movement to assess magnitude height and width of fusion initiating component, or measure ratio of convergence to divergence peak velocity at different initial vergence angles.

15. The method of claim 9, wherein the plurality of oculomotor characteristics is weighted.

16. The method of claim 9, wherein the trained machine learning model is a first trained machine learning model, wherein a second trained machine learning module is used to render the visual stimulus with the head mounted display or to adjust the visual stimulus to elicit the response from the visual system of the user.

17. A non-transitory computer-readable medium storing instructions that when executed by a processing device causes the processing device to implement a method for performing an assessment of oculomotor function of a user, the method comprising:
- rendering visual stimulus with a head mounted display using a stereoscopic effect;
- adjusting the visual stimulus to elicit a response from a visual system of the user wearing the head mounted display;
- objectively measuring at least a subset of a plurality of oculomotor characteristics of the user based at least on the response;
- based on the objective measurement of the at least the subset of the plurality of oculomotor characteristics of the user, dynamically adjusting the rendering of the visual stimulus to a non-linear program sequence, using a trained machine learning model, to reduce at least one of a duration of an oculomotor function assessment and resources required to complete the oculomotor function assessment; and
- generating the oculomotor function assessment by combining the at least the subset of the plurality of oculomotor characteristics;
- wherein the dynamic adjustment of the rendering of the visual stimulus using the trained machine learning model does not reduce the sensitivity of the oculomotor function assessment despite the reduced assessment duration and/or the resources required to complete the oculomotor function assessment.

18. The medium of claim 17, wherein the method further comprises:
- measuring movement of the user's eyes via the head mounted display; and
- transmitting a measure of movement of the user's eyes to the processing device.

19. The medium of claim 18, wherein adjusting the visual stimulus is based on the measure of movement.

20. The medium of claim 18, wherein objectively measuring the at least the subset of the plurality of oculomotor characteristics is based on the measure of movement.

21. The medium of claim 17, wherein the plurality of oculomotor characteristics includes at least one of a near point of convergence, dissociated and associated phoria, fixation disparity, saccades, smooth pursuit, binocular endurance, fusional range, or vergence facility.

22. The medium of claim 17, wherein the plurality of oculomotor characteristics include at least one of vergence peak velocity, accuracy, response amplitude, latency, time to peak velocity, time constant, error, variance, asymmetry between left and right eye movement, ramp respond speed, dissection of movement to assess magnitude height and width of fusion initiating component, or measure ratio of convergence to divergence peak velocity at different initial vergence angles.

23. The medium of claim 17, wherein the plurality of oculomotor characteristics is weighted.

24. The medium of claim 17, wherein the trained machine learning model is a first trained machine learning model, wherein a second trained machine learning module is used to render the visual stimulus with the head mounted display or to adjust the visual stimulus to elicit the response from the visual system of the user.

* * * * *